United States Patent [19]

Kee Woo et al.

[11] 3,970,643
[45] July 20, 1976

[54] 5''-AMINO-3',5''-DIDEOXYBUTIROSIN A AND DERIVATIVES

[75] Inventors: Peter Wing Kee Woo; Theodore Herbert Haskell, both of Ann Arbor, Mich.

[73] Assignee: Parke, Davis & Company, Joseph Campau at the River, Mich.

[22] Filed: Apr. 17, 1975

[21] Appl. No.: 569,129

[52] U.S. Cl. .................................. 536/17; 424/180
[51] Int. Cl.[2] .......................................... C07H 15/22
[58] Field of Search .................. 260/210 AB, 210 K

[56] References Cited
UNITED STATES PATENTS 3,828,021   8/1974   Beattie et al. ................ 260/210 AB

OTHER PUBLICATIONS

B371,085, Jan. 1975, Naito et al. 260/210 AB.
Ikeda et al., "Jour. Antibiotics," vol. XXVI, No. 5, 1973, pp. 307–309.

*Primary Examiner*—Johnnie R. Brown

[57] ABSTRACT

O-2,6-diamino-2,3,6-trideoxy-α-D-ribo-hexopyranosyl-(1 → 4)-O-[5-amino-5-deoxy-β-D-xylofuranosyl-(1 → 5)]-N$^1$-[(S)-4-amino-2-hydroxy-1-oxobutyl]-2-deoxystreptamine), also named 5''-amino-3',5''-dideoxybutirosin A and acid addition salts of said compounds. These compounds exhibit a wide spectrum of antibacterial activity.

The above compounds can be produced from O-2,6-dideoxy-2,6-bis(Z-amino)-α-D-glucopyranosyl-(1 → 4)-O-[2,3-di-O-acetyl-5-deoxy-5-(Z-amino)-β-D-xylofuranosyl-(1 → 5)]-6-O-acetyl-N$^1$-[(S)-2-acetyloxy-1-oxo-4-(Z-amino)butyl]-2-deoxy-N$^3$-streptamine, also named protected 5''-amino-deoxybutirosin A by treating said compound with trifluoromethanesulfonic anhydride and pyridine to yield the 3'-O-(trifluoromethanesulfonyl) compound. The product is reacted with the sodium salt of an arylmercaptan and the resulting 3'-arylthio compound is purified and treated with ammonia, thus deprotecting the four hydroxy groups. Lastly, the five amino groups are deprotected and the arylthio group is removed by a reductive cleavage.

2 Claims, No Drawings

5''-AMINO-3',5''-DIDEOXYBUTIROSIN A AND DERIVATIVES

SUMMARY AND DETAILED DESCRIPTION

The present invention relates to new chemical compounds and to methods for their production. More specifically, this invention relates to O-2,6-diamino-2,3,6-trideoxy-α-D-ribo-hexopyranosyl-(1 → 4)-O-[5-amino-5-deoxy-β-D-xylofuranosyl-(1 → 5)]-N¹-[(S)-4-amino-2-hydroxy-1-oxobutyl]-2-deoxystreptamine); also named 5''-amino-3',5''-dideoxybutirosin A and to acid addition salts thereof. 5''-Amino-3',5''-dideoxybutirosin (I) may be represented by either structure I*a* or I*b*.

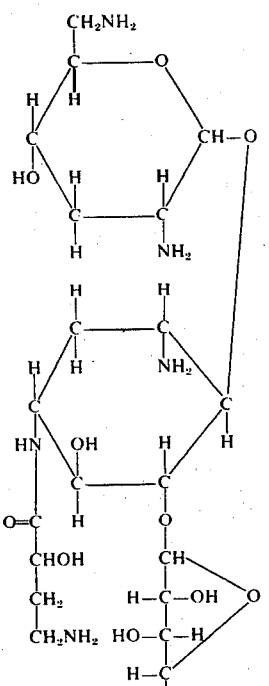

I*a*

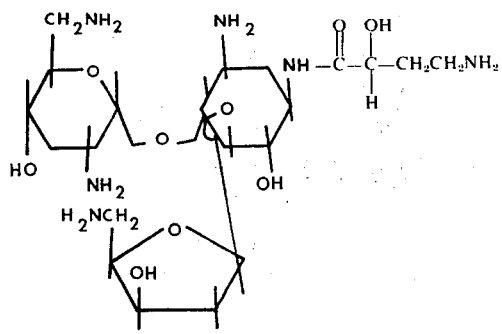

I*b*

In addition, this invention relates to methods for the preparation of 5''-amino-3',5''-dideoxybutirosin A (I) from a N-protected-arylthio-dideoxybutirosin A compound and salts thereof.

More specifically, the invention relates to the preparation of 5''-amino-3',5''-dideoxybutirosin A (I) by the reduction of a 5''-amino-penta-N-protected-3'-arylthio-3',5''-dideoxybutirosin A compound having the formula

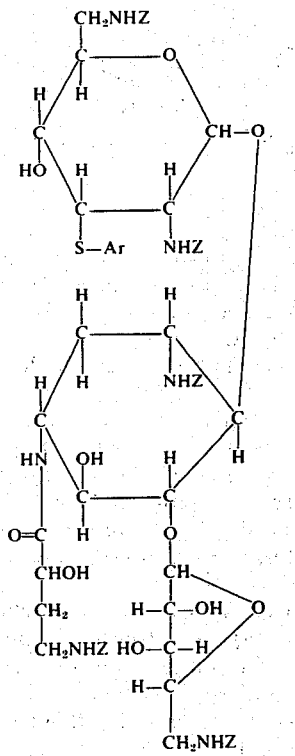

II wherein Z is a protective group which is readily removed by reduction, preferably a group of the formula

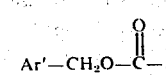

wherein Ar' is an aryl group such as

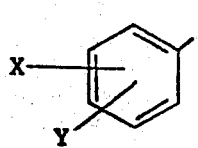 , 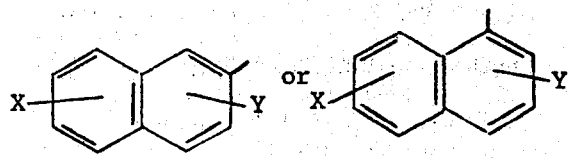

wherein X or Y is hydrogen, halogen, nitro, lower alkyl of from one to four carbon atoms, lower alkoxy of from one to four carbon atoms, etc., the most preferred group represented by

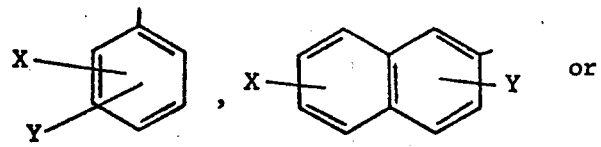

is carbobenzoxy, and Ar is a group such that the group ArS is readily removed by reduction, preferably Ar is an aryl group of the formula

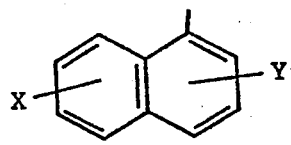

wherein X or Y is hydrogen, halogen, nitro, lower alkyl of from one to four carbon atoms, lower alkoxy of from one to four carbon atoms, etc. The most preferred group is where Ar is phenyl.

The reduction may be achieved either catalytically or chemically.

The catalytic reduction is carried out using hydrogen in the presence of a noble metal catalyst, such as platinum, palladium, etc., optionally supported on a carrier such as charcoal or barium sulfate, the preferred catalyst being palladium oxide on barium sulfate which is transformed by hydrogen to palladium metal on barium sulfate.

The hydrogen pressure that the reaction is conducted under is not critical and generally pressures of from about one to about three atmospheres are employed.

Most standard solvents used in catalytic hydrogen reactions may be employed, although water miscible, non-reactive solvents are preferred. These include lower alkanols of from one to three carbon atoms, lower alkanoic acids of from one to three carbon atoms, tetrahydrofuran, dioxane and mixtures of these. A preferred solvent is a methanol-acetic acid mixture. The presence of an acid in the reaction mixture is desirable so that the progress of the reaction can be measured by carbon dioxide evolution, indicating reductive cleavage of the carbobenzoxy groups.

While the temperatures and times are not critical, the reaction is generally conducted at about room temperature (20°–30°C) until, under acid conditions, there is no further carbon dioxide evolution and the removal of the phenylthio group is complete, as indicated by thin layer chromatography (about 10 to about 30 hours).

While at a minimum, sufficient hydrogen is needed to compltely reductively cleave the carbobenzoxy groups and the phenylthio group, a large quantity of catalyst is required, generally from 300 percent to 500 percent based on the weight of compound II.

The compound of the invention having structure Ia may be isolated as the free base or converted to an acid addition salt by reaction with an acid such as hydrochloric acid, sulfuric acid, phosphoric acid, pamoic acid, carbonic acid, etc., and isolated as such.

Another method for the conversion of a 5''-amino-penta-N-protected-3'-ArS-3',5''-dideoxybutironsin A (II) into compound I utilizes a sodium in liquid ammonia reaction.

This reaction is generally carried out at the boiling point (−33°C) of the solvent liquid ammonia; however, lower temperatures may be employed, such as carrying out the reaction in a dry ice-acetone bath (approximately −60°C).

Sodium is added until a transient blue color appears which lasts for from 30 seconds to about one minute.

The product may be isolated in the form of the free base or converted to an acid addition salt by reaction with an acid such as hydrochloric acid, sulfuric acid, phosphoric acid, pamoic acid, etc.

The compounds of the formula II are prepared from their corresponding O-protected compounds having the formula III.

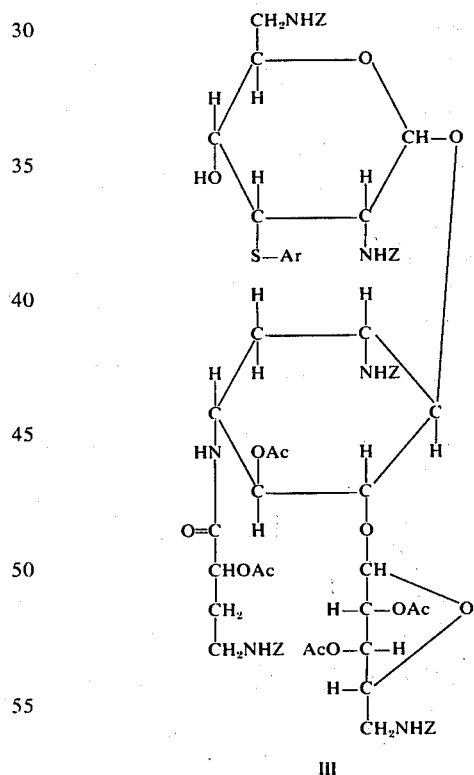

III wherein Ar and Z are as previously defined for compounds of the formula II and Ac is acetyl.

The tetra-O-acetyl-5''-amino-penta-N-protected-3'-ARS-3',5''-dideoxybutirosin A (III) is dissolved in anhydrous methanol. Anhydrous ammonia is bubbled into this solution for approximately 8 minutes with the temperature being maintained at about 0°C. The solution is then allowed to stand for about 18 hours at 0°C followed by removal of the solvent to give the starting material of the formula II.

The compounds of the formula III are prepared from a mixture consisting of a major proportion of a tetra-O-acetyl-5''-amino-penta-N-protected-5''-deoxy-3'-O-(trifluoromethanesulfonyl)butirosin A (IV) and a minor proportion of a tetra-O-acetyl-5''-amino-penta-N-protected-5''-deoxy-4'-O-(trifluoromethanesulfonyl)butirosin A (V), wherein the compounds of formula III are ultimately formed from the compounds of formula IV.

In addition to the formation of compound III, a second compound having the formula VI is also formed.

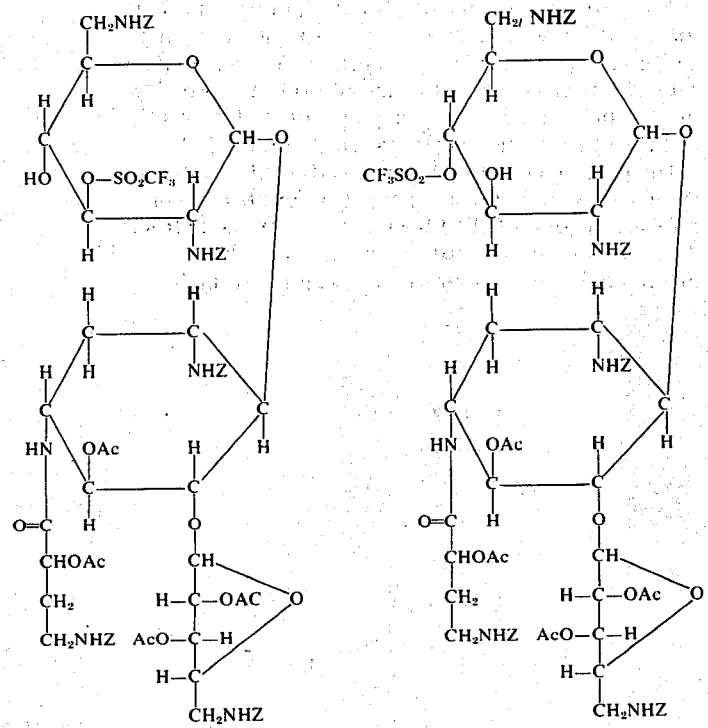

wherein Ar, Z and Ac are as defined for compounds of the formula III.

The mixture comprising compounds of the formulae IV and V, wherein the compounds of formula IV comprise the major portion of the mixture, is added to a sodium thiophenol in dry dimethylformamide at −5°C and then stirred for 16 hours at 5°C. After neutralization with acetic acid and dilution with chloroform, the reaction medium is filtered, concentrated to a syrup in vacuo, dissolved in chloroform, washed with water, aqueous sodium bicarbonate, water, saturated aqueous sodium chloride and dried. The resulting solution is passed through a silica gel column which is next eluted with 2 per cent methanol in chloroform, thus yielding two fractions, one being a compound of the formula III and the other being a compound of the formula VI.

The mixture comprising compounds of the formulae IV and V, wherein the compounds of formula IV comprise the major portion of the mixture, is prepared from 2'',2''',3'',6-tetra-O-acetyl-5''-amino-penta-N-protected-5''-deoxybutirosin A having the formula

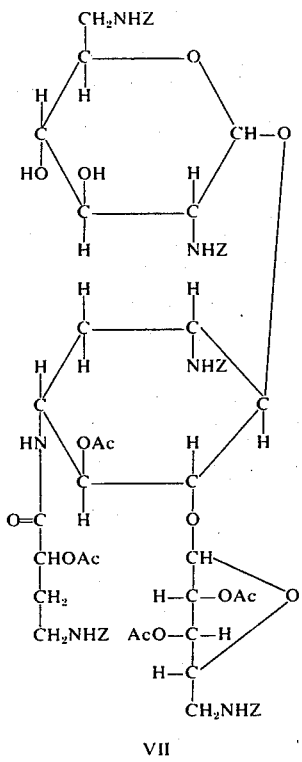

VII

Trifluoromethanesulfonic acid anhydride in dichloromethane is added to a mixture of compound VII and pyridine in dichloromethane over about a 2 hour period with the temperature being held at about −5°C. The reaction mixture is diluted with additional dichloromethane, washed with water, dilute hydrochloric acid, water, saturated aqueous sodium bicarbonate, water and saturated sodium chloride. After drying and removal of solvent, a product is obtained which is a mixture of compounds IV and V.

Compounds of the formula VII are prepared according to the following procedure. A 2'',2''',3'',6-tetra-O-acetyl-5''-amino-penta-N-protected-3',4'-O-cyclohexylidene-5''-deoxybutirosin A compound of the formula

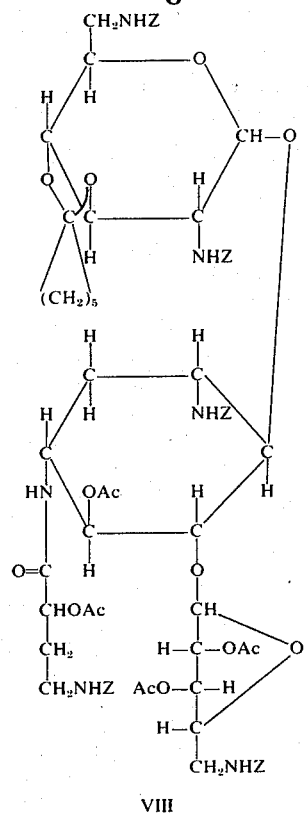

VIII wherein Z and Ac are as previously defined for compounds of the formulae III and VI, dissolved in glacial acetic acid is hydrolysed by the addition of water at 20°–30°C for about 5 hours. This procedure is described in co-pending U.S. application Ser. No. 503,991, filed Sept. 6, 1974.

In addition, the application, which is incorporated by reference discloses the preparation of a compound of the formula VIII. The grouping Z may be any readily removable protective group which is prepared by methods known to those skilled in the art.

The compounds of this invention form acid-addition salts with any of a variety of inorganic and organic acids. Pharmaceutically-acceptable acid-addition salts are formed with such acids as hydrochloric, hydrobromic, sulfuric, phosphoric, acetic, succinic, citric, maleic, malic, carbonic, gluconic, pamoic and related acids. The invention includes acid-addition salts generally as any toxic salt can be converted to the free base or to a pharmaceutically-acceptable salt. The free base and the acid-addition salt forms are intercovertible by adjustment of the pH or by the use of ion-exchange resins. They differ in solubility properties, but except as noted above are otherwise equivalent for purposes of the invention.

In addition, the compounds of this invention and their acid-addition salts can exist in anhydrous forms as well as in solvated, including hydrated, forms. In general, the hydrated forms and the solvated forms with pharmaceutically-acceptable solvents are equivalent to the anhydrous or unsolvated form for the purposes of the invention.

The compounds of this invention and their acid-addition salts possess antibacterial activity. They show activity when tested by well-recognized in vitro anti-bacterial screening procedures. The following table shows typical results obtained from such procedures expressed in terms of the minimal concentration required to inhibit the growth of each of a number of representative bacterial species.

Thus, the compounds of this invention and their acid-addition salts are of value for their antibacterial activity against a number of microorganisms and especially against *Pseudomonas aeruginosa* and certain microorganisms resistant to butirosin. They can be administered either parenterally or topically. They can also be used to sterilize the gastrointestinal tract by oral administration.

Because of their wide antibacterial spectrum, the compounds of the invention are also useful as antibacterial agents in in vitro applications such as sterilizing laboratory instruments and surfaces, sterilizing pharmaceutical products, and maintaining sterile conditions during pharmaceutical manufacturing operations. For sterilizing laboratory instruments and surfaces and similar in vitro applications, the compounds can be used in the form of a 0.1 to 1.0% aqueous solution.

|  | MIC $\mu$/ml* | |
|---|---|---|
|  | Butirosin $H_2SO_4$ | I-carbonate |
| Staph auretis S18713[a] | 100 | 3.1 |
| Klebs. pneumoniae MGH-1 | 3.1 | 6.3 |
| Serr. marcescens IMM-5 | 25 | 25 |
| Entero. cloacae IMM-50 | 3.1 | 6.3 |
| Pseudo. aerug. No. 28 | 12.5 | 1.6 |
| " VAD12-7-7 | 12.5(6.3) | 3.1 |
| " 74C-1 | 25 (12.5) | 3.1 |
| " 733 | 12.5 | 3.1 |
| " LA-3399 | 100 (50) | 12.5 |
| " UI-18 | 25 (12.5) | 3.1 |
| " Aquilar[a] | >200 | 12.5 |
| " G-76[b] | 25 (50) | 12.5 |
| " 58.38 | 12.5 (25) | 3.1 |
| Esch. coli JR-76.2[b] | >200 | 25 |
| Pseudo. aerug. 130[c] | 25 | 6.3 |

*Microtitration in TSB
[a]Butirosin resistant
[b]Butirosin and Gentamicin resistant
[c]Gentamicin resistant

EXAMPLE 1

A slurry of 69 mg. of 20% palladium oxide on barium sulfate in 1 ml. of methanol saturated with hydrogen is added to a solution of 318 mg. of 5''-amino-penta-N-carbobenzoxy-3'-phenylthio-3',5''-dideoxybutirosin A in 7 ml. of methanol and 2 ml. of 2N acetic acid in 1 ml. of methanol saturated with hydrogen. The mixture is stirred at room temperature while hydrogen gas is bubbled through the reaction mixture until carbon dioxide evolution ceases. An additional 50 mg. of 20% palladium oxide on barium sulfate suspended in 1 ml. of methanol, saturated with hydrogen, is added and hydrogenolysis is continued. The addition of 50 mg. of 20% palladium oxide on barium sulfate in 1 ml. of methanol, followed by hydrogenolysis, is repeated several times until there is no further evolution of carbon dioxide and until thin layer chromatography shows the absence of an ultraviolet-absorbing component, which indicates complete reaction. The catalyst is removed by filtration and the filtrate is passed through a 26 ml. column of a carboxymethyl dextran (Carboxymethyl Sephadex) in the ammonium ion form. The column is washed with water, then eluted with an aqueous gradient of 0.2N to 0.8N. The eluate is collected in fractions of about 5 ml. Those fractions giving a positive reaction to the phenol-sulfuric acid test are combined, concentrated at reduced pressure and finally freeze-dried to give 5''-amino-3',5''-dideoxybutirosin A.

The free base is dissolved in water and solid carbon dioxide is added to a final pH of 6.8. The resulting solution is freeze-dried to give a residue of a carbonate salt. Optical rotations as a 1% solution in water are shown to be the following:

| $\lambda$ | 589 | 578 | 546 | 436 | 365 |
|---|---|---|---|---|---|
| $[\alpha]^{23}$ | +18 | +18.5 | +22.4 | +36.4 | +48.4 |

A solution of 35.4 mg. of the free base in 1 ml. of water is treated with 0.1N sulfuric acid (about 2.5 ml.) until a pH of 6.28 is attained. Optical rotations as a 0.94% solution in water are as follows:

| $\lambda$ | 589 | 578 | 546 | 436 | 365 |
|---|---|---|---|---|---|
| $[\alpha]^{23}$ | +13.8 | +15.5 | +17.6 | +28.8 | +42.3 |

EXAMPLE 2

Freshly cut pieces of metallic sodium are added with stirring to a solution of 200 mg. of 5''-amino-penta-N-carbobenzoxy-3'-phenylthio-3',5''-dideoxybutirosin A in 40 ml. of liquid ammonia until a blue color persists for about 30 seconds. Solid ammonium chloride (107 mg.) is added and the excess ammonia allowed to evaporate at room temperature, the last traces being removed at reduced pressure. The residue is dissolved in water, the pH is adjusted to 6–7 with hydrochloric acid and the solution extracted with ether. The aqueous solution is passed through a column of 10 ml. of a weak cation exchange resin (Amberlite IRC-50) in the ammonium form. The column is washed with water and eluted with 1N aqueous ammonia. The eluate is concentrated at reduced pressure and finally freeze-dried to give 5''-amino-3',5''-dideoxybutirosin A.

STARTING MATERIALS

For convenience and clarity, various chemical intermediates referred to in this section are identified by the "butirosin" terminology as explained elsewhere herein.

To a stirred solution of 5.006 g. of aminodeoxybutirosin A (U.S. Pat. No. 3,784,541) in 18.75 ml. of water at 0°C. is added 35 ml. of methanol, followed by 10.111 g. of sodium bicarbonate. The mixture is stirred in an ice-water bath while 12.0 ml. of benzyl chloroformate (95%) is added dropwise during 30 minutes in 1 ml. portions, each portion being followed by 5 ml. of cold methanol. The mixture is stirred an additional 5 hours at 5°C., then treated dropwise with 6.0 ml. of pentylamine and stirred at 5°C. for 16 hours. A solution of 3.0 ml. of acetic acid in 13.5 ml. of methanol is then added slowly and the mixture is filtered, the filter cake being washed with methanol. The filtrate and washings are combined and evaporated at reduced pressure. The residual oil is triturated several times with ether, then dissolved in 150 ml. of chloroform. The chloroform solution is washed several times with water, dried and evaporated to give 5''-amino-penta-N-carbobenzoxy-5''-deoxy-butirosin A. Thin layer chromatography (10% methanol in chloroform) on silica gel plate (Quanta Q1F, 10 cm. length) showed one major spot, $Rf = 0.50$.

To a solution of 2.692 g. of 5''-amino-penta-N-carbobenzoxy-5''-deoxybutirosin A in 27 ml. of dry dimethylformamide, in a round bottom flask with a sidearm, is added 160 mg. of p-toluenesulfonic acid monohydrate and 2.0 ml. of 1,1-dimethoxycyclohexane. The flask is fitted with a coil condenser, the top of which is connected through a stopcock to a vacuum of 15 mm.

Hg. The side-arm is fitted with a very fine capillary through which dry air is allowed to bubble into the solution. With the system at 15 mm. Hg pressure, the flask is heated at 50°C. for 34 minutes, then allowed to stand at room temperature for 10 minutes. The vacuum is removed and, after 40 minutes, 0.5 ml. of triethylamine is added. The mixture is evaporated at reduced pressure and the residue is dissolved in 9 ml. of chloroform. The chloroform solution is chromatographed on a column of silica gel (54 g., 1.9 cm. × 44 cm.) packed in chloroform. The column is eluted in sequence with the following solvents: (1) 190 ml. of chloroform; (2) 200 ml. of 1% methanol in chloroform; (3) 200 ml. of 2% methanol in chloroform; (4) 200 ml. of 4% methanol in chloroform; (5) 200 ml. of 6% methanol in chloroform; (6) 250 ml. of 8% methanol in chloroform; and (7) 250 ml. of 12% methanol in chloroform. The eluate is collected in fractions of about 20 ml. each. Those fractions showing a single spot of $Rf$ 0.65 by thin layer chromatography (silica gel plate — Quanta Q1F, 10 cm. length), using 10% methanol in chloroform, are combined and evaporated at reduced pressure to give a residue of 5''-amino-penta-N-carbobenzoxy-3',4'-O-cyclohexylidene-5''-deoxy-butirosin A.

A solution of 417 mg. of 5''-amino-penta-N-carbobenzoxy-3',4'-O-cyclohexylidene-5''-deoxybutirosin A in 3.2 ml. of pyridine and 0.8 ml. of acetic anhydride is allowed to stand at room temperature for 23 hours, then evaporated at reduced pressure. The residue of 2'',2''',3'',6-tetra-O-acetyl-5''-amino-penta-N-carbobenzoxy-3',4'-O-cyclohexylidene-5''-deoxybutirosin A is dried at reduced pressure over potassium hydroxide.

With stirring, 0.8 ml. of water is added to a solution of 491 mg. of 2'',2''',3'',6-tetra-O-acetyl-5''-amino-penta-N-carbobenzoxy-3',4'-O-cyclohexylidene-5''-deoxybutirosin A in 3.2 ml. of glacial acetic acid. (The starting material identified is the compound of a foregoing formula in which Z is (phenylmethoxy)carbonyl, Ac is acetyl and n is 5). The mixture is allowed to stand at 20°–30°C. for 4.7 hours, then evaporated at reduced pressure to give a residue of 2'',2''',3'',6-tetra-O-acetyl-5''-amino-penta-N-carbobenzoxy-5''-deoxybutirosin A which is dried at reduced pressure over potassium hydroxide.

Thin layer chromatography (3% methanol in chloroform) on silica gel plate (Quanta Q1F, 10 cm. length) showed one major spot, $Rf = 0.28$. The observed melting range was 69°–112°C. Infrared absorption maxima in a potassium bromide disc were observed at: 605, 700, 740, 778, 915, 1030 (shoulder), 1043, 1068 (shoulder), 1135, 1240, 1308, 1342, 1375, 1458, 1500 (shoulder), 1532, 1588, 1710, 1745 (shoulder), 2945, 3035, 3068, 3092, 3360–3430. Optical rotations as 1.03% solution in methanol were determined as follows:

| $\lambda$ | 589 | 578 | 546 | 436 | 365 |
|---|---|---|---|---|---|
| $[\alpha]^{23}$ | +16.9 | +17.5 | +19.8 | +34.2 | +54.7 |

Tetra-O-acetyl-5''-amino-penta-N-carbobenzoxy-5''-deoxy-3'-O-(trifluoromethanesulfonyl)butirosin A and Tetra-O-acetyl-5''-amino-penta-N-carbobenzoxy-5''-deoxy-4'-O-(trifluoromethanesulfonyl)butirosin A.

A solution of 2.18 ml. of trifluoromethanesulfonic acid anhydride in 70 ml. of dichloromethane is added dropwise to a solution of 6.66 g. of 2'',2''',3'',6-tetra-O-acetyl-5''-amino-penta-N-carbobenzoxy-5''-deoxybutirosin A in 70 ml. of dichloromethane and 12 ml. of pyridine, with stirring at −5°C. over a period of 1.75 hours. The solution is stirred an additional hour at −5°C., then diluted with 250 ml. of dichloromethane. The resulting solution is washed successively with 25 ml. of water, 2.0 N hydrochloric acid until acidic, 50 ml. of water, 40 ml. of saturated aqueous sodium bicarbonate, 50 ml. of water and 50 ml. of saturated aqueous sodium chloride, then dried and evaporated at reduced pressure to give a residue consisting of a major proportion of tetra-O-acetyl-5''-amino-penta-N-carbobenzoxy-5''-deoxy-3'-O-(trifluoromethanesulfonyl)butirosin A and a minor proportion of tetra-O-acetyl-5''-amino-penta-N-carbobenzoxy-5''-deoxy-4'-O-(trifluoromethanesulfonyl)butirosin A.

Tetra-O-acetyl-5''-amino-penta-N-carbobenzoxy-3'-phenylthio-3',5''-dideoxybutirosin A and Tetra-O-acetyl-5''-amino-penta-N-carbobenzoxy-4'-phenylthio-4',5''-dideoxybutirosin A.

A stirred solution of 1.5 g. of a 50% mineral oil dispersion of sodium hydride in 15 ml. of dry dimethylformamide is treated dropwise under nitrogen at 5°C. with 4.5 ml. of thiophenol. The solution is stirred 2 hours at room temperature, cooled to −5°C. and 7.2 g. of a mixture consisting of a major proportion of tetra-O-acetyl-5''-amino-penta-N-carbobenzoxy-5''-deoxy-3'-O-(trifluoromethanesulfonyl)butirosin A and a minor proportion of tetra-O-acetyl-5''-amino-penta-N-carbobenzoxy-5''-deoxy-4'-O-(trifluoromethanesulfonyl)butirosin A is added. The solution is diluted with 16 ml. of dimethylformamide and stirred for 16 hours at 5°C. The resulting mixture is treated with 2 ml. of acetic acid, diluted with 200 ml. of chloroform and filtered. The filtrate is evaporated at reduced pressure and the residue is dissolved in chloroform. The chloroform solution is washed successively with water, aqueous sodium bicarbonate, water and saturated aqueous sodium chloride, then dried. The solution is passed over a silica gel column (150 g.) and the column is washed with chloroform until free of thiophenol. The column is eluted with 2% methanol in chloroform and the eluate is collected in fractions of about 3 ml. each.

Those fractions showing a single spot of $Rf$ 0.50 by thin layer chromatography (silica gel plate —Quanta Q1F, 10 cm. length), using 2% methanol in chloroform, are combined and evaporated at reduced pressure to give a residue of tetra-O-acetyl-5''-amino-penta-N-carbobenzoxy-3'-phenylthio-3',5''-dideoxybutirosin A.

Those intermediate fractions containing both components are combined and further purified by preparative thin layer chromatography on silica gel plate to give tetra-O-acetyl-5''-amino-penta-N-carbobenzoxy-3'-phenylthio-3',5''-dideoxybutirosin A (Rf 0.50).

5''-Amino-penta-N-carbobenzoxy-3'-phenylthio-3',-5''-dideoxybutirosin A.

Anhydrous ammonia is bubbled into a solution of 307 mg. of tetra-O-acetyl-5''-amino-penta-N-carbobenzoxy-3'-phenylthio-3',5''-dideoxybutirosin A in 20 ml. of anhydrous methanol at 0°C. for 8 minutes. The solution is allowed to stand at 0°C. for 18 hours, then evaporated at reduced pressure to give a residue of 5''-amino-penta-N-carbobenzoxy-3'-phenylthio-3',-5''-dideoxybutirosin A.

We claim :

1. A member of the class consisting of O-2,6-diamino-2,3,6-trideoxy-α-D-ribo-hexopyranosyl-(1 → 4)-O-[5-amino-5-deoxy-β-D-xylofuranosyl-(1 → 5)]-N$^1$-[(S)-4-amino-2-hydroxy-1-oxobutyl]-2-deoxystreptamine and pharmaceutically acceptable acid addition salts thereof.

2. The compound of claim 1 having the name O-2,6-diamino-2,3,6-trideoxy-α-D-ribo-hexopyranosyl-(1 → 4)-O-[5-amino-5-deoxy-β-D-xylofuranosyl-(1 → 5)]-N$^1$-[(S)-4-amino-2-hydroxy-1-oxobutyl]-2-deoxystreptamine.

* * * * *